United States Patent [19]
Berkley

[11] Patent Number: 5,490,195
[45] Date of Patent: Feb. 6, 1996

[54] METHOD FOR MEASURING AND EXTENDING THE SERVICE LIFE OF FATIGUE-LIMITED METAL COMPONENTS

[75] Inventor: Stanley G. Berkley, Jupiter, Fla.

[73] Assignee: Fatigue Management Associates LLC, Palos Verdes Estates, Calif.

[21] Appl. No.: 245,011

[22] Filed: May 18, 1994

[51] Int. Cl.$^6$ .................................................. G01N 23/20
[52] U.S. Cl. ................................................ 378/72; 378/70
[58] Field of Search ................................. 378/58, 70, 71, 378/72, 57

[56] References Cited

U.S. PATENT DOCUMENTS

| | | | |
|---|---|---|---|
| 3,762,885 | 10/1973 | Speirs et al. | 29/196.2 |
| 4,034,585 | 7/1977 | Straub | 72/53 |
| 4,191,599 | 3/1980 | Stickels et al. | 148/16.5 |
| 5,125,016 | 6/1992 | Korhonen et al. | 378/72 |
| 5,272,746 | 12/1993 | Isobe et al. | 378/72 |

OTHER PUBLICATIONS

"A Review of Nondestructive Methods for Residual Stress Measurement" Clayton O. Ruud, pp. 35–39, Jul. 1981.
"Successful Applications; TEC portable X–ray residual Stress analysis systems"; Technology for Energy Corporation, pp. 1–10, Jan. 1991.
"X–ray Diffraction Stress Analysis as an NDE·Technique"; Pardue, 8 sheets, 1993.
Suresh, S., "Some Design Considerations and Case Studies," *Fatigue of Metals*, Cambridge University Press, New York, 1991, pp. 499–502.
Flyer for "AST S2001, X–Ray Stress Analyzer," American Stress Technologies, Inc., Pittsburgh, Pa.
Flyer for "AST S2002, X–Ray Stress Analyzer," American Stress Technologies, Inc., Pittsburgh, Pa.
Flyer for "The TEC 1600 Series Stress Analysis System", The TEC Stress Analysis Group, Knoxville, Tenn.
Meguid, S. A., *Impact Surface Treatment*, International Conference on Impact Treatment Processes (2d: 1986: Cranfield Institute of Technology).
Daly, J. J., "Status of Controlled Shot–Peening Technology in the United States", Metal Improvement Company, Paramus, New Jersey, pp. 237–241.
Taira, S. et al., "Local Residual Stress Near Fatigue Crack Tip", *Transactions ISU*, vol. 19, 1979, pp. 411–418. Parly published in *Journal of The Society of Materials Science, Japan*, 27 (1978), 251, in Japanese. English Version Jul. 18, 1978.
Delitizia, A. T., "Improving Fatigue Life Through Advanced Shot Peening Techniques", *Manufacturing Engineering*, May 1984, pp. 85–87.
Kirk, D., "Residual Stresses and Retained Austenite in Shot Peened Steels", First International Conference on Shot Peening, Paris 14–17 Sep. 1981, pp. 271–277.
Coulon, A., "Effect Of The Honing Drum Upon The Inducement Of Compressive Residual Stresses," *Journal of Mechanical Working Technology*, 8 (1983) pp. 161–169.

(List continued on next page.)

*Primary Examiner*—David P. Porta
*Assistant Examiner*—Don Wong
*Attorney, Agent, or Firm*—Fitch, Even, Tabin & Flannery

[57] ABSTRACT

Improved methods for managing a population of metal components subject to fatigue failure are provided. The residual compressive stress in the critical surfaces of such components, especially in areas of high stress concentration, are measured non-destructively using x-ray diffraction techniques. The measured residual compressive stress is used as a management criteria. A component having a residual compressive stress greater than a predetermined value can be returned to service. However, once the measured residual compressive stress of a component galls below the predetermined value, it can either be removed permanently from service, or it can be reworked to increase its residual compressive stress and then returned to service. Additionally, by measuring the residual compressive stress of an individual component, the remaining service life of that individual component can be estimated. These methods for management of populations of such metal components allow for increasing the service life of the components in a safe and effective manner.

36 Claims, 1 Drawing Sheet

OTHER PUBLICATIONS

Harting, M., and G. Fritsch, "A Non-destructive Method to Determine the Depth-Dependence of Three-dimensional Residual Stress States by X-ray Diffraction," *J. Phys. D: Appl. Phys.*, 26 (1993) pp. 1814–1816.

Kuhn, H. A., "An X-Ray Study of Creep-Deformation Induced Changse of the Lattice Mismatch in the gamma-Hardened Monocrystalline Nickel-Base Superalloy SRR 99", *Asta Metall. Mater.*, vol. 39, No. 11, pp. 2783–2794, 1991.

METHOD FOR MEASURING AND EXTENDING THE SERVICE LIFE OF FATIGUE-LIMITED METAL COMPONENTS

FIELD OF THE INVENTION

This invention generally relates to a method for managing the service life of fatigue-limited metal components. This invention also generally relates to a method for managing and extending the service life of fatigue-limited metal components. More specifically, this invention is related to a management method using a non-destructive technique for measuring the remaining useful service life of fatigue-limited metal components by determining the residual compressive stress in the critical surfaces of the individual components. Using the method of this invention, a metal component is either removed from service or reworked to increase its residual compressive stress once the residual compressive stress is reduced or falls below a predetermined value. This invention allows an increase in both safety and economy in the management and operation of turbine engines and other machines containing fatigue-limited metal components by providing a reliable means for non-destructively measuring the remaining service life of the fatigue-limited metal components. This invention is especially adapted for managing populations of fatigue-limited rotating parts in gas turbine engines, including aircraft engines, and the like. Using the present methods of this invention to manage and measure the residual compressive stress in such parts or components, it is now possible to determine the appropriate time (i.e., prior to permanent deterioration from residual tensile stress crack initiation) for reworking the part to increase or restore its residual compressive stress so that the service life of the part or component can be extended. Using the present methods of this invention, the overall service life of a population of components used in, for example, jet engines or turbine engines, can be maximized without a significant decease in safety. In fact, the present invention can provide both increased safety and economy for the aviation and other industries.

BACKGROUND OF THE INVENTION

Fatigue-limited metal components of gas turbines or jet engines, or other machine components subject to metal failure or fatigue, must be carefully managed in order to avoid failure during operation. The failure, for example, of a critical component of a jet engine during operation may result in loss of life or other catastrophic consequences. Currently in the aviation industry (commercial and military), there are three general types of management techniques or approaches used for the management of fatigue-limited machine components in order to prevent possible catastrophic failure due to metal fatigue. Each of these approaches attempts to balance safety and economic concerns based on available data. See, for example, S. Suresh, *Fatigue of Metals*, 499–502 (1991), which generally discusses the three commonly used management approaches.

The most conservative of these approaches, often termed the "safe life" approach, is based on the estimated fatigue life established through analysis and comparable experience by the engine manufacturer. This approach attempts to estimate the point at which the shortest-lived part or component in the total population would be expected to fail. After allowing for a suitable safety margin, an arbitrary retirement point is adopted for that component. This retirement point is normally measured in total take-off cycles or hours. Once a part reaches the retirement point, it is removed from service and mutilated to prevent further, unauthorized use. Although generally allowing for the greatest margin of safety, significant economically useful service life of such parts is lost. In effect, this "safe life" approach is based on, and controlled by, an estimation of the lifetime of the weakest part or component in the total population.

A somewhat less conservative management technique is the so-called "fail safe" approach. In this approach, a maximum service life is determined by the total accumulated service hours or cycles (whichever is shorter) at which the first crack is detected in an actual part (i.e., disk or drum rotor used in a compressor, turbine, or engine) in the population of like parts. Once a part has developed such a crack, its accumulated service life (in hours or cycles) is effectively used to determine the service life of all similar parts in the population. If a part is later found to develop a crack at an earlier time, then that part is then used to redefine (and shorten) the acceptable service life limits of the population. Once a part reaches its acceptable service life, it is removed from service and mutilated to prevent further use. In effect, this "fail safe" approach is also based on, and controlled by, the actual weakest part or component in the total population. Many parts may still have many hours of safe and useful service life remaining beyond that of this weakest part. But, since the useful and safe service life of these parts cannot be reliably determined, they must be removed from service in the interest of safety. This "fail safe" approach is generally used in the airline industry for mature fleets where low cycle fatigue cracks have been detected in the relevant component populations. Where sufficient service data has not been developed, the more conservative "safe life" approach is generally used. In each approach, however, parts having many remaining hours of safe and reliable use will be removed from service.

More recently, the United States Air Force has successfully adopted an even less conservative management technique, the so-called "retirement for cause" approach, for its management of some critical engine components. In this approach, the parts are periodically examined non-destructively for cracks using, for example, fluorescent dye penetration or magnaflux techniques. Once a crack is observed, that part, but only that part, is immediately retired from service. Other parts, even though they may have accumulated service times equal to or greater than the retired part, are continued to be used until they actually develop cracks. To operate safely, this approach requires periodic and frequent inspections of the individual parts. In general, as parts age, the frequency of inspections should be increased. In any event, the frequency of inspections must be such that the period between inspections is less, preferably by a significant margin, than the time normally required for a detectable crack to further deteriorate to the point of actual failure. Although this approach may result in more frequent teardowns for inspection of the individual parts, the potential savings based on achieving, or at least approaching, the maximum lifetimes of the individual parts can be enormous. The major drawback of this approach is that it relies upon detection of an actual crack in the part. Thus, this approach is generally not suitable for parts in which crack formation cannot be detected in a reliable and consistent manner. Once a crack has formed, the part contains, in effect, a permanent, irreversible defect which will ultimately lead to failure, perhaps catastrophic failure, unless that part is removed from service in a timely manner. Additionally, this approach, of course, is not suitable for use where the normal time between the initial development of a detectable crack and failure of the part is relatively short. Moreover, in parts where actual failure normally does not follow quickly after the development of a crack, if such a crack develops shortly after an inspection, the risk of failure during actual operation increases simply because the length of time in which the part is operated with the defect is maximized. Therefore, this method has an increased safety risk when compared to the "safe life" and "fail safe" approaches. This increased risk, although perhaps small, may still be significant because the detection point is the actual formation of a detectable crack. The longer that part remains in service, once a crack has formed, the greater the risk of catastrophic failure.

It would be desirable, therefore, to provide non-destructive methods to measure the remaining service or useful life of fatigue-limited metal components before crack initiation has begun or, at least, before actual cracks can be observed (i.e., before permanent and irreversible damage has begun). It would also be desirable to provide methods by which the service or useful life of fatigue-limited metal components could be increased without significantly increasing the risk of catastrophic failure of the metal components during operation. Such methods would provide both increased safety and economy for the aviation industry (commercial and military). The methods of this invention generally provide such improved methods.

SUMMARY OF THE INVENTION

The present invention relates to methods for the management of populations of fatigue-limited metal components. This invention also relates to methods for the detection of the remaining service life of individual fatigue-limited metal components. The metal components to be managed by the present invention include metal components having relatively high levels of residual compressive stress as manufactured and which are subject to fatigue-related failure. The relatively high residual compressive stress of such a metal component as manufactured may be the result of the actual manufacture process used and/or subsequent working of the metal component by shot peening or other cold working processes after actual production to increase the residual compressive stress. Preferably, the residual compressive stress as manufactured is in the range of about 50,000 to 200,000 pounds per square inch and, more preferably, in the range of about 150,000 to 180,000 pounds per square inch. Components having residual compressive stresses higher or lower than these ranges can, of course, be managed by the methods of the present invention. However, the components as manufactured should have sufficient residual compressive stress for their intended use. Using the methods of this invention, increases in both safety and economy in the management of such metal components is expected.

Fatigue failures in metal components almost always develop from cracks generated in the surface layer of the metal components exposed to high stress environments. To reduce the likelihood of crack formation, great care is normally taken in the manufacture of such metal components to ensure that the initial residual stress in the critical surface layers of the crystalline structure of the metal are in relatively high compression (often up to 170,000 pounds per square inch or higher). During operation under conditions of high load and operating temperatures, the residual compressive stress of the component gradually diminishes over time. Once the residual compressive stress reaches zero, the trend continues and builds up residual tensile stress in these areas. Over time, the residual tensile stress can increase to levels in excess of the ultimate tensile strength of the surface of the material and cracks develop. Such cracks in a component left in service propagate until they reach a critical length, at which time catastrophic failure occurs. The present invention provides methods for managing metal components whereby conditions involving significant residual tensile stress and, therefore, crack initiation are avoided. By monitoring the residual compressive stress in areas of high stress concentration and maintaining the metal component under conditions of compressive stress, the present invention provides a management program which does not rely on either expected or actual crack formation as the management criteria.

In the method of this invention, a non-destructive technique (i.e., x-ray diffraction) is used to measure the remaining residual compressive stress in the relevant metal components. Once the residual compressive stress of an individual component falls below a predetermined value, that part, but only that part, is effectively flagged for further attention. For metal components having residual compressive stress below a predetermined value, there are essentially two options. In the first option, the metal components is simply removed permanently from service. In the second option, the metal component is reworked (using, for example, shot peening) to increase its residual compressive stress and then returned to service. By periodically evaluating such metal components using the methods of this invention, the service life of the total population of metal components can be maximized in a safe and efficient manner.

For metal components having residual compressive stress higher than the predetermined value, the remaining service life of that component can be determined. The greater the difference between the measured residual compressive stress and the predetermined value, the greater the remaining service life for that component should be. Such information should be useful (especially as considerable historical data for the population becomes available over time) in matching components for use in particular engines or applications (i.e., matching components which have comparable remaining service life) or for scheduling routine teardowns and maintenance.

One object of the present invention is to provide a method for managing a population of metal parts in order to determine when to remove an individual metal part from service, wherein said metal parts are manufactured having relatively high levels of residual compressive stress and said metal parts are subject to fatigue-related failure, said method comprising:

(1) selecting an individual metal part from the population;

(2) determining the remaining residual compressive stress of the surface of the selected individual metal part in one or more areas of stress concentration using x-ray diffraction techniques; and (3) removing the selected individual metal part from service if the remaining residual compressive stress measured in one or more areas of stress concentration has fallen below a predetermined level.

Another object of the present invention is to provide a method for managing a population of metals parts in order to extend the service life of individual metal parts in the population, wherein said metal parts are manufactured having relatively high levels of residual compressive stress and said metal parts are subject to fatigue-related failure during service, said method comprising, for each individual metal part in the population:

(1) removing the individual metal part from the population from service;

(2) measuring the remaining residual compressive stress of the surface of the individual metal part in one or more areas of stress concentration using x-ray diffraction techniques;

(3) comparing the remaining residual compressive stress measured in one or more areas of stress concentration to a predetermined level; and (4) if the remaining residual compressive stress remains above the predetermined level, returning the individual metal part to service; or (5) if the remaining residual compressive stress is at or below the predetermined level, reworking the individual metal part to increase the residual compressive stress to a reworked level above the predetermined level and then returning the individual metal part to service.

Although the present invention is preferably directed towards methods for the management of large populations of similar type metal parts, it can also be used to test individual metal parts. Thus, for example, the present invention can also be used for spot checking metal parts throughout their expected service life as part of routine or scheduled preventive maintenance or during repairs or teardown procedures necessitated by breakdowns. Thus, still another object of the present invention is to provide a method for determining when to remove a metal part from service, wherein said metal part is manufactured having relatively high levels of residual compressive stress and said metal part is subject to fatigue-related failure, said method comprising:

(1) measuring the remaining residual compressive stress of the surface of the metal part in one or more areas of stress concentration using x-ray diffraction techniques;

(2) comparing the remaining residual compressive stress measured in one or more areas of high stress concentration to a predetermined value; and (3) removing the metal part from service if the remaining residual compressive stress measured in one or more areas of stress concentration is less than the predetermined level.

Still another object of the present invention is to provide a method for extending the service life of a metal part, wherein said metal part is manufactured having relatively high levels of residual compressive stress and said metal part is subject to fatigue-related failure during service, said method comprising:

(1) measuring the remaining residual compressive stress of the surface of the metal part in one or more areas of stress concentration using x-ray diffraction techniques;

(2) comparing the remaining residual compressive stress measured in one or more areas of stress concentration to a predetermined level; and (3) if the remaining residual compressive stress remains above the predetermined level, returning the metal part to service; or (4) if the remaining residual compressive stress is at or below the predetermined level, reworking the metal part to increase the residual compressive stress to a reworked level above the predetermined level and then returning the metal part to service.

These and other objects and advantages of the present invention will be apparent from a consideration of the present specification and drawing.

DETAILED DESCRIPTION OF THE INVENTION

The invention generally relates to methods for managing the service life of fatigue-limited metal components and to methods for managing and extending the service life of fatigue-limited metal components. The methods of this invention employ a non-destructive technique for measuring the remaining useful service life of fatigue-limited metal components by determining the residual compressive stress in the critical surfaces of the individual component. The residual compressive stress can be correlated with the remaining service life of the individual component. If the residual compressive stress has not fallen below a predetermined value, the component can be returned to service. If the residual compressive stress reaches or falls below a predetermined value, the component can be permanently removed from service. Or, if desired and appropriate, the component can be reworked to increase the residual compressive stress to a level above the predetermined value, preferably a value approaching the compressive stress of the component as originally manufactured, and then returned to service.

Figure 1:
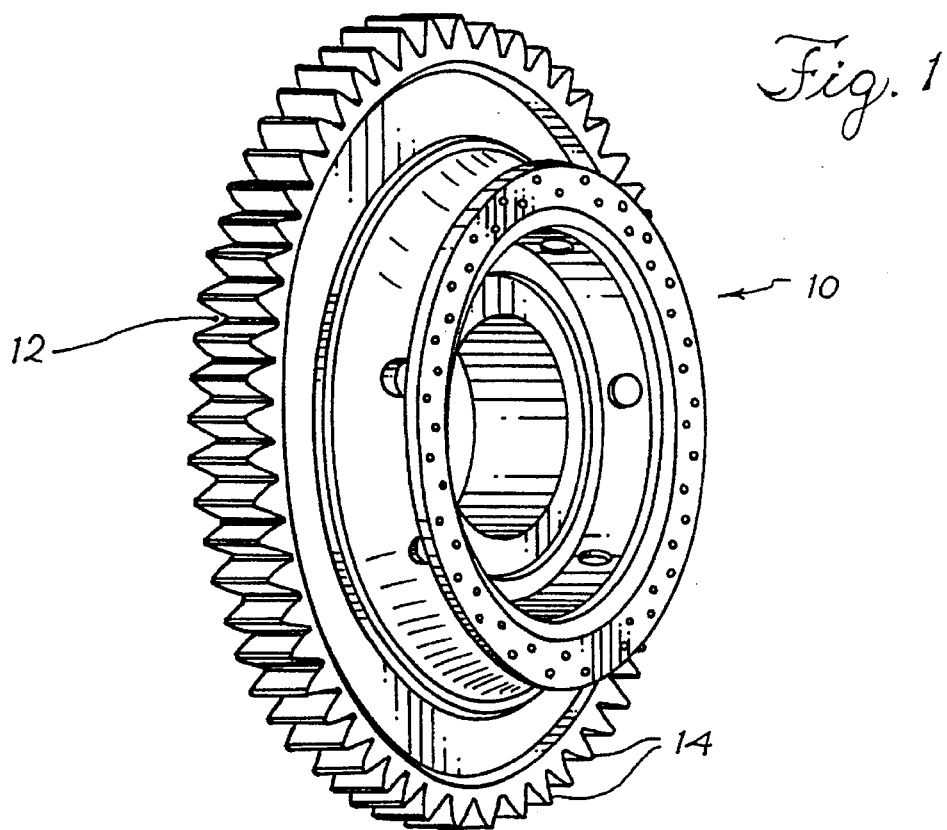
FIG. 1 illustrates a typical disk from a jet engine showing areas of stress concentration in which residual compressive stress should be determined.
Figure 2:
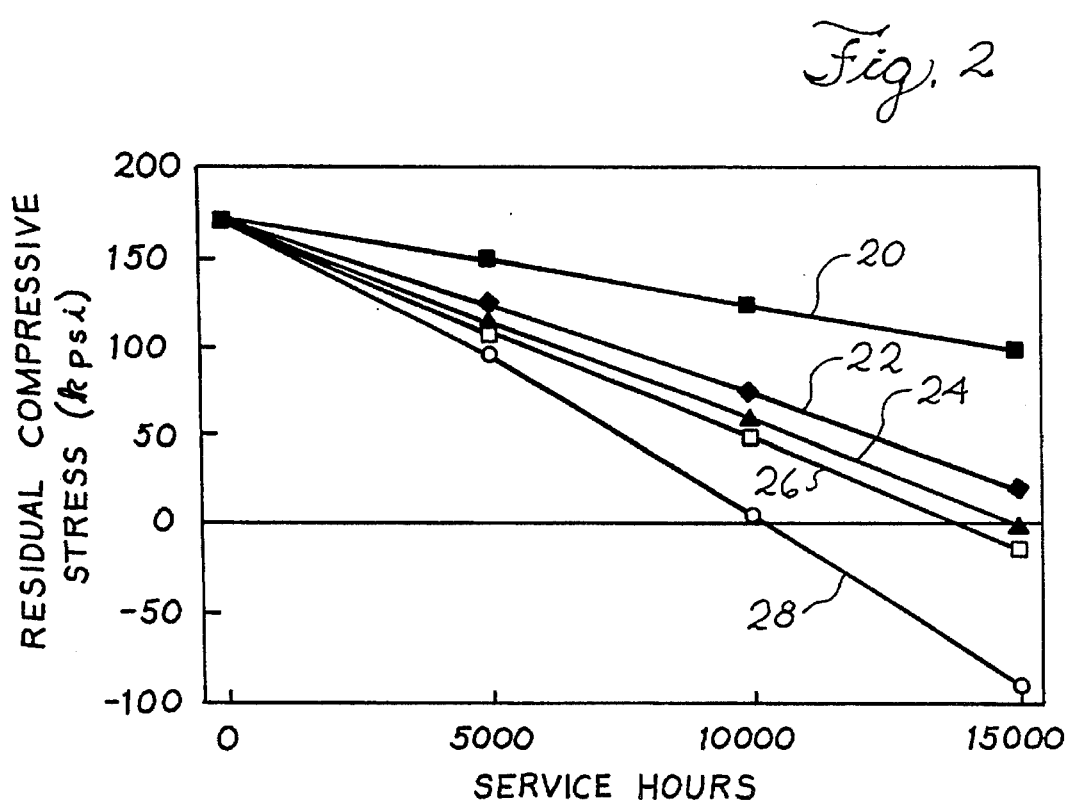
FIG. 2 shows a typical plot of residual compressive stress as a function of service hours for turbine disks operating under different load and temperature conditions.

It is well established that fatigue failures develop from cracks generated in the surface layer of metal components exposed to high stress environments. For example, failure normally occurs because of cracks forming in areas of stress concentration in such components. FIG. 1 illustrates such a component, specifically a disk 10 for use in a gas turbine engine. Failure of such a disk is often caused by cracks forming in the surface layers of areas of high stress concentration such as the inside radii or bottom 12 of dovetail or firtree slots 14. These dovetail or firtree slots are used for attachment of the compressor and turbine blades (not shown). To reduce the likelihood of crack formation, great care is normally taken in the manufacture of such components to ensure that the initial residual stress in the critical surface layers of the crystalline structure of the metal are in high compression. For example, turbine disks, such as the one illustrated in FIG. 1, are generally manufactured with residual compressive stress in the order of about 170,000 pounds per square inch. During operation in a turbine engine (i.e., conditions of high load and operating temperatures), the residual compressive stress gradually diminishes over time as shown in FIG. 2. The curves in FIG. 2 (labeled 20, 22, 24, 26, and 28) are for different turbine disks 10 (i.e., different stages) used in a gas turbine engine. In such an engine, each disk is subjected to different load and temperature conditions during operation. Thus, the rate of decrease of the residual compressive stress is different for each disk or stage. Once the residual compressive stress reaches zero, residual tensile stress can build up in these areas. Over time, the residual tensile stress can increase to levels in excess of the ultimate strength of the surface of the material and cracks will initiate. Such cracks in a component left in service propagate until they reach a critical length, at which time catastrophic failure will occur.

The methods of this invention monitor the residual compressive stress in areas of stress concentration in order to prevent the initial formation of cracks in the surface. By removing the component from service before the stresses change from compressive to tensile in nature or by maintaining the stress in compression, the present methods allow individual components to be used in a manner in which surface cracks are not formed or are, at least, formed at a significantly lower rate as compared to current management methods. The present methods allow for achievement of the maximum service life of components without increased failure or safety risks. Moreover, the present methods allow for significantly extending the service life of individual components without increased failure or safety risks.

In practice, for a given type and population of metal components, the residual compressive stress in the surface layer of the individual component is measured in one or more areas of stress concentration using x-ray diffraction techniques. The actual area measured is normally in the range of about ¼ by ¼ inches to about 1 by 1 inch, although smaller or larger areas can be used if desired. The measured value (or values or averaged value) is compared to a predetermined value. If the measured value is above the predetermined value, the part can be returned to service. If however, the measured value equals or falls below this predetermined value, the component can be treated in several ways. In a first option, the component can be permanently removed from service. In such cases, it is generally preferred that the component be mutilated, or otherwise marked, to prevent further, unauthorized use. In a second option, the component can be reworked to increase its residual compressive stress and then returned to service. Normally, such a component can be reworked and returned to service a fixed number of times or cycles (i.e., until other failure mechanisms predominate or the component no longer meets design criteria or specifications). The acceptable number of cycles for reworking such components will generally be determined on a case-by-case basis. For a given component, such as the disk shown in FIG. 1, the cycle of service and reworking can generally be repeated so long as the component retains its dimensional and microstructural stability.

In some cases when the residual compressive stress is above, but close to or approaching, the predetermined value, it may be preferred to rework that part at that time rather than wait for the residual compression stress to fall below the predetermined value. For example, if the measured residual compressive stress suggests that the part has only a relatively short service life remaining before reworking will be required (see, for example, curve 22 in FIG. 2 at 15,000 hours with a predetermined value of zero pounds per square inch), it may be more economical to rework the part during the current scheduled shutdown/teardown event rather that put the part back in service and then require an unscheduled teardown to rework it only a short time later. Whether this modified approach is appropriate and desirable in a given case will depend, in larger part, on the expected service life before that part will fall below the predetermined value. If the expected remaining service life is short (thereby necessitating a unscheduled teardown for remeasurement), it may be more economical to rework that part even though it has remaining service life. In such a case, the predetermined value is effectively increased for that part only.

As one skilled in the art will realize, the predetermined value of the residual compressive stress for any given population of components will depend, at least in part, on the residual compressive stress of the components as originally manufactured, the specific physical and metallurgical characteristics of the components, the environment in which the components are used, and any appropriate safety factors. For populations of different parts, this predetermined value will likely be different because of different designs of the parts and exposure to different stresses during use. Populations of the same parts, but operated under different conditions and environments, may also have different predetermined values. Moreover, for a given component, different areas of stress concentration may have different predetermined values. For example, different areas of metal component will normally be exposed to, or will experience, different levels of stress and may, therefore, experience changes in the compressive stress at different rates. In such cases, the area that reaches its predetermined value first will normally control the disposition of that component. Although not necessary, it will generally be preferred that the initial compressive residual stress of the metal components be measured or otherwise known before they are placed in service, or shortly thereafter. Measurement of the residual compressive stress of a component as originally manufactured can help insure that only components meeting specifications are used and can provide benchmarks for later measurements of remaining residual compressive stress. Moreover, such initial residual compressive stress data, along with the data generated by the present methods, can be used to define or redefine component specifications and design criteria as appropriate.

The predetermined value can be expressed in terms of absolute numbers (e.g., a specific value in suitable units for the residual compressive stress) or in relative numbers (e.g., a percentage of the remaining compressive stress of the component as compared to the residual compressive stress as originally manufactured). Moreover, the predetermined value for a given population may change over time as more historical data becomes available. For example, for newly designed components, it may be desirable to use a relatively high predetermined value to guard against unexpected failures for increased safety. As service life data becomes available, however, it may be appropriate to decrease the predetermined value if significant safety or failure related problems are not found in the population. By carefully adjusting the predetermined value for a given population of components over time, it should be possible to approach the optimum value while maintaining operational safety.

In some cases, a predetermined value of about zero pounds per square inch (or other appropriate units) or 100 percent decrease in residual compressive stress (i.e., the point at which stress moves from compressive to tensile in nature) may be appropriate. The use of zero pounds per square inch or 100 percent decrease as the management criteria might, for example, be appropriate to maximize the service life of a component where reworking the component is not practical or is otherwise not anticipated. In most cases, however, a predetermined value of a value greater than zero pounds per square inch or less than 100 percent decrease will generally be preferred and appropriate based on safety considerations. Such higher predetermined values will be especially preferred where reworking of the component to restore all or part of the residual compressive stress is anticipated. In some cases, however, a predetermined value of less than zero pounds per square inch or greater than 100 percent decrease may be appropriate.

As noted above, the residual compressive stress is measured non-destructively using conventional x-ray diffraction techniques. Preferably, the residual compressive stress is measured using portable x-ray diffraction equipment. Examples of such x-ray equipment and techniques can be found in U.S. Pat. No. 5,125,016 (Jun. 12, 1992); Taira & Tanaka, "Residual Stress Near Fatigue Crack Tips," 19 *Transactions of the Iron & Steel Institute of Japan*, 411–18 (1979); Harting & Fritsch, "A Non-destructive Method to Determine the Depth-dependence of Three-dimensional Residual Stress States by X-ray Diffraction," 26 *J. Phys. D: Appl. Phys.*, 1814–16 (1993); Kuhn et al., "An X-ray Study of Creep-deformation Induced Changes of the Lattice Mismatch in γ'-Hardened Monocrystalline Nickel-Base Superalloy SRR 99," 39 *Acta Metall. Mater.*, 2783–94 (1991), all of which are hereby incorporated by reference. Portable x-ray equipment, which is generally preferred in the present invention, can be obtained commercially from, for example, Technology for Energy Corporation (P.O. Box 22996, Lexington Drive, Knoxville, Tenn. 37933) or American Stress Technologies, Inc. (61 McMurray Road, Pittsburgh, Pa. 15241). Other types and designs of x-ray diffraction equipment or techniques can also be used in the present invention. Normally such measurements should be made, at a minimum, during scheduled teardowns and other maintenance events. In some cases, however, it may be desirable to make such measurements more often than regularly scheduled maintenance events, especially during the early service life of a population of newly designed components lacking a extensive service life history. Normally, such measurements of the residual compressive stress will be made on the individual parts during teardowns. For some components, however, it may be possible to make the necessary measurements without having to perform complete teardowns. As noted above, x-ray diffraction measurements of residual compressive stress should be made in areas of high stress concentration (e.g., the bottom 12 of the firtree slots 14 on the disk 10 shown in FIG. 1). Generally, areas of high stress concentration are those areas in which crack formation has been observed or is more likely to occur. It is not necessary, however, to make such measurements in each and every area of high stress concentration in a given component, especially where such areas are operated under similar load and temperature conditions. For the disk in FIG. 1, for example, measurements might be taken on the bottom 12 of the firtree slots 14 located at 0, 90, 180, and 270 degrees, rather than at the bottom of every slot 14. The individual measurements at these representative locations, or an average of the individual measurements, are compared to the predetermined value. As the database develops, the number and location of measurements for a given disk (or other population of components) can be modified as appropriate.

Once a component reaches or falls below its predetermined value, it can either be removed permanently from service or reworked to increase its residual compressive stress to a level above the predetermined value and then returned to service. For example, using a predetermined value of zero pounds per square inch, the disk represented by curve 28 in FIG. 2 should be removed from service or reworked after about 10,000 hours of service; the disks represented by curves 24 and 26 should be removed from service or reworked after about 15,000 hours; the disks represented by curves 20 (especially) and 22 (to a lesser extent) have service lives greater than 15,000 hours. Preferably, the residual compressive stress in such reworked components is returned to a level approaching the original residual compressive stress as manufactured. Reworking such components can be carried out using conventional procedures for increasing or achieving residual compressive stress. Such methods include, for example, shot peening and other methods of cold working the surface (e.g., hammer peening, rolling, or burnishing methods). See, for example, Daly, "Status of Controlled Shot-Peening Technology in the United States," International Conference on Impact Treatment Processes (2nd: 1986) in *Impact Surface Treatment* (Meguid, Ed.), 237–41; Delitizia, "Improving Fatigue Life Through Advanced Shot Peening Techniques," 92 Manufacturing Engineering, 85–87 (1984). Of course, such reworking must be carried out before any permanent deterioration occurs from residual stress cracking. Thus, where such reworking is anticipated, the predetermined value used as the management criteria preferably is higher (i.e., a higher predetermined value of residual compressive stress) than in cases where reworking is not anticipated. By setting the management criteria higher in such cases, one moves further away from the condition where crack formation, which may not even be detectable, may occur, thereby providing an increased margin of safety. It is generally preferred that reworking increases the residual compressive stress to at least 50 percent of the residual compressive stress in the part as originally manufactured. More preferably, the rework level for the residual compressive stress is at least 80 percent of the value as originally manufactured. Even more preferably, the reworked level is comparable to the value as originally manufactured.

The methods of this invention generally allow one to maximize the service life of a metal component by providing a procedure to determine when to optimally rework the metal component to restore all or part of the residual compressive stress. Excessive reworking can actually decrease the service life since reworking techniques such as shot peening increase the dimension of the metal part in the reworked area. Thus, the likelihood of a metal component moving out of its design specification increases as a function of the number of times it is reworked. The present invention provides procedures whereby the maximum service life can be obtained with the minimum number of reworkings. Of course, the effect of reworking on dimensional stability should be taken into account when establishing the appropriate predetermined value for a given component.

The present methods for management of population of metal components provide considerable improvement over management methods currently in use. Both the "safe life" and "fail safe" methods rely on expected service life based on either predicted values or statistical values of crack formation in the weakest component in the population. In these methods, service life is not evaluated for individual components. Thus, the vast majority of components are retired while still possessing useful and significant service life. The "retirement for cause" approach relies on the observation of actual crack formation in a given component. Once crack formation is observed, that component is removed from service. Unfortunately, once crack formation can be observed, the component cannot be rehabilitated or reworked for additional service life. Additionally, at least in some cases, waiting for actual crack formation as a management criteria can result in significant safety risks. The methods of the present invention provide improved management procedures by providing management criteria (i.e., residual compressive stress compared to predetermined values) which are observable well before irreversible crack initiation or formation occurs. Using the methods of the present invention, the maximum service life of such components can be obtained in a safe and effective manner. Using the methods of the present invention, at least some components can be reworked to increase the residual compressive stress and placed back in service, thereby providing increased efficiency without compromising safety. In fact, the methods of the present invention are expected to achieve improved efficiency and improved safety as compared to the management methods currently in use since the management criteria is based on residual compressive stresses rather than on actual or expected crack formation. By using residual compressive stress as the management criteria, rather than actual or expected crack formation, the margin of safety is expected to be increased, perhaps significantly.

The methods of the present invention are ideally suited for augmenting computer tracking of metal components during their service life. Moreover, the data generated from the present methods (i.e., residual compressive stress) and data regarding the service life and history of individual components can be used to develop a management database for the metal components. As the historical basis of such a database grows, it will be possible to reliably predict the service life of a given part. Thus, once such a database is developed, one will not need to measure the compressive stress of each and every component during each teardown or other maintenance event. If the total service life or history of the component is sufficiently short (as determined from the historical data in the database), measurement of the compressive stress can be delayed. Only such components having a service life or history approaching some definable parameter (again as determined from the historical data in the database) will be required to have the actual compressive stress measured and compared to the predetermined value. For example, for a given component, the database might show that only components having a service live in excess of 10,000 hours ever have residual compressive stresses approaching or below the predetermined value. In such a case, only components with service lives greater than this value will need to have the residual compressive stress measured during a routine teardown. Of course, components with abnormalities or components subjected to extreme service events should be evaluated regardless of the cumulated service life. Moreover, it may still be prudent to at least perform some spot checks on components with shorter service lives in order to confirm the continuing validity of the database and its predictive ability. By avoiding actual measurements for components very unlikely to have residual compressive stress values lower than the predetermined value, considerable savings can be obtained. Of course, the method used to predict this likelihood must be proven over time to be both effective and safe.

The present methods are not, however, intended to replace all non-destructive testing of such metal components. As those skilled in the art will realize, the present methods are designed to manage failures and defects related to crack initiation mechanisms commonly associated with the residual compressive stress and residual tensile stress levels in the surface layers. Other non-destructive testing methods for identifying other types of failures and/or failure mechanisms, especially early in the service life of such components (i.e., during the so-called "infant mortality" period), should be continued as appropriate. Incorporation of such data from other non-destructive testing procedures in the management database discussed above may allow even more complete tracking and management of populations of such metal components.

Additionally, using the methods of this invention, components of approximately equal remaining service life (i.e., approximately equal residual compressive stress) can be used together. Normally, the frequency of such teardowns in individual engines will be controlled by the component having the shortest remaining service life. By avoiding use of components of widely varying remaining service life, early teardown of engines, necessitated by a single component with only a short remaining service life, can be avoided. By matching components with similar remaining service lives in a given engine, the frequency of teardowns over the entire population can be reduced.

That which is claimed is:

1. A method for managing a population of metal parts in order to determine when to remove an individual metal part from service, wherein said metal parts are manufactured having relatively high levels of residual compressive stress and said metal parts are subject to fatigue-related failure, said method comprising:

(1) selecting an individual metal part from the population;

(2) determining the remaining residual compressive stress of the surface of the selected individual metal part in one or more areas of stress concentration using x-ray diffraction techniques; and (3) removing the selected individual metal part from service if the remaining residual compressive stress measured in the one or more areas of stress concentration has fallen below a predetermined level.

2. A method as defined in claim 1, wherein the predetermined level of the remaining residual compressive stress is about zero.

3. A method as defined in claim 1, wherein the predetermined level of the remaining residual compressive stress is a fixed percentage less than 100 percent of the residual compressive stress in the part as manufactured.

4. A method as defined in claim 1, wherein the metal parts are rotating parts used in a gas turbine or jet engine.

5. A method as defined in claim 4, wherein the metal parts are disks or drum rotors.

6. A method as defined in claim 1, wherein the remaining residual compressive stress measurements, generated over time, for the individual parts in the population of parts are used to form a database that can be used for predicting the service life of a given part in order to determine whether, and when, that given part should be selected from the population for determining the remaining residual compressive stress for that given part.

7. A method as defined in claim 1, wherein the residual compressive stress levels of the individual parts as manufactured are known and wherein the residual compressive stress levels of the individual parts as manufactured and the remaining residual compressive stress measurements, generated over time, for the individual parts in the population of parts are used to form a database.

8. A method as defined in claim 7, wherein the residual compressive stress levels of the individual parts as manufactured are measured prior to, or shortly after, the individual parts are initially placed into service.

9. A method as defined in claim 7, wherein said database is used to help define or redefine specifications or design criteria for the individual parts.

10. A method for managing a population of metals parts in order to extend the service life of individual metal parts in the population, wherein said metal parts are manufactured having relatively high levels of residual compressive stress and said metal parts are subject to fatigue-related failure during service, said method comprising, for each individual metal part in the population:

(1) removing the individual metal part from the population from service;

(2) measuring the remaining residual compressive stress of the surface of the individual metal part in one or more areas of stress concentration using x-ray diffraction techniques;

(3) comparing the remaining residual compressive stress measured in the one or more areas of stress concentration to a predetermined level; and (4) if the remaining residual compressive stress remains above the predetermined level, returning the individual metal part to service; or (5) if the remaining residual compressive stress is at or below the predetermined level, reworking the individual metal part to increase the residual compressive stress to a reworked level above the predetermined level and then returning the individual metal part to service.

11. A method as defined in claim 10, wherein steps (1) through (5) are repeated periodically for the individual metal part until the individual metal part must be permanently removed from service.

12. A method as defined in claim 10, wherein the predetermined level of the remaining residual compressive stress is a fixed percentage less than 100 percent of the residual compressive stress in the part as manufactured.

13. A method as defined in claim 10, wherein the metal parts are rotating parts used in a gas turbine or jet engine.

14. A method as defined in claim 13, wherein the metal parts are disks or drum rotors.

15. A method as defined in claim 10, wherein the reworked level is at least 50 percent of the residual compressive stress level of the metal parts as manufactured.

16. A method as defined in claim 14, wherein the reworked level is at least 80 percent of the residual compressive stress level of the metal parts as manufactured.

17. A method as defined in claim 10, wherein the reworked level is about the same as the residual compressive stress level of the metal parts as manufactured.

18. A method as defined in claim 14, wherein the reworked level is about the same as the residual compressive stress level of the metal parts as manufactured.

19. A method as defined in claim 10, wherein the remaining residual compressive stress measurements, generated over time, for the individual parts in the population of parts are used to form a database that can be used for predicting the service life of a given part in order to determine whether, and when, that given part should be selected from the population for determining the remaining residual compressive stress for that given part.

20. A method as defined in claim 10, wherein the residual compressive stress levels of the individual parts as manufactured are known and wherein the residual compressive stress levels of the individual parts as manufactured and the remaining residual compressive stress measurements, generated over time, for the individual parts in the population of parts are used to form a database.

21. A method as defined in claim 20, wherein the residual compressive stress levels of the individual parts as manufactured are measured prior to, or shortly after, the individual parts are initially placed into service.

22. A method as defined in claim 20, wherein said database is used to help define or redefine specifications or design criteria for the individual parts.

23. A method for determining when to remove a metal part from service, wherein said metal part is manufactured having relatively high levels of residual compressive stress and said metal part is subject to fatigue-related failure, said method comprising:
(1) measuring the remaining residual compressive stress of the surface of the metal part in one or more areas of stress concentration using x-ray diffraction techniques;
(2) comparing the remaining residual compressive stress measured in the one or more areas of high stress concentration to a predetermined value; and
(3) removing the metal part from service if the remaining residual compressive stress measured in the one or more areas of stress concentration is less than the predetermined level.

24. A method as defined in claim 23, wherein the predetermined level of the remaining residual compressive stress is about zero.

25. A method as defined in claim 23, wherein the predetermined level of the remaining residual compressive stress is a fixed percentage less than 100 percent of the residual compressive stress in the metal part as manufactured.

26. A method as defined in claim 23, wherein the metal part is a rotating part used in a gas turbine or jet engine.

27. A method as defined in claim 26, wherein the metal part is a disk or drum rotor.

28. A method for extending the service life of a metal part, wherein said metal part is manufactured having relatively high levels of residual compressive stress and said metal part is subject to fatigue-related failure during service, said method comprising:
(1) measuring the remaining residual compressive stress of the surface of the metal part in one or more areas of stress concentration using x-ray diffraction techniques;
(2) comparing the remaining residual compressive stress measured in the one or more areas of stress concentration to a predetermined level; and
(3) if the remaining residual compressive stress remains above the predetermined level, returning the metal part to service; or
(4) if the remaining residual compressive stress is at or below the predetermined level, reworking the metal part to increase the residual compressive stress to a reworked level above the predetermined level and then returning the metal part to service.

29. A method as defined in claim 28, wherein steps (1) through (4) are repeated periodically for the metal part until the metal part must be permanently removed from service.

30. A method as defined in claim 28, wherein the predetermined level of the remaining residual compressive stress is a fixed percentage less than 100 percent of the residual compressive stress in the metal part as manufactured.

31. A method as defined in claim 28, wherein the metal part is a rotating part used in a gas turbine or jet engine.

32. A method as defined in claim 31, wherein the metal part is a disk or drum rotor.

33. A method as defined in claim 28, wherein the reworked level is at least 50 percent of the residual compressive stress level of the metal part as manufactured.

34. A method as defined in claim 32, wherein the reworked level is at least 80 percent of the residual compressive stress level of the metal part as manufactured.

35. A method as defined in claim 28, wherein the reworked level is about the same as the residual compressive stress level of the metal part as manufactured.

36. A method as defined in claim 32, wherein the reworked level is about the same as the residual compressive stress level of the metal part as manufactured.

* * * * *